United States Patent
Chandra et al.

(10) Patent No.: US 6,651,014 B2
(45) Date of Patent: Nov. 18, 2003

(54) APPARATUS FOR AUTOMATICALLY MEASURING THE RESISTIVITY OF SEMICONDUCTOR BOULES BY USING THE METHOD OF FOUR PROBES

(75) Inventors: Mohan Chandra, Merrimack, NH (US); David M. Darling, Amherst, NH (US); L. Dolan Roman, Nashua, NH (US); Carl P. Chartier, Manchester, NH (US); Glen Alan Burgess, Hudson, NH (US)

(73) Assignee: G.T. Equipment Technologies, Inc, Merrimack, NH (US)

( * ) Notice: Subject to any disclaimer, the term of this patent is extended or adjusted under 35 U.S.C. 154(b) by 0 days.

(21) Appl. No.: 10/138,835

(22) Filed: May 3, 2002

(65) Prior Publication Data

US 2002/0177962 A1 Nov. 28, 2002

Related U.S. Application Data

(60) Provisional application No. 60/288,337, filed on May 3, 2001.

(51) Int. Cl.$^7$ .............................................. G01N 27/04
(52) U.S. Cl. .......................... 702/65; 702/57; 324/715; 324/719
(58) Field of Search ............................. 702/65, 57, 47, 702/50, 108, 117, 118, 119, 123, 113–115, 138, 140, 132, 136, 127, 183, 188, 150, 152, 157, 158, FOR 171, FOR 103–FOR 106, FOR 123, FOR 124, FOR 127, FOR 128, FOR 134, FOR 136, FOR 141–FOR 143, FOR 144, FOR 146, FOR 147, FOR 170, 64; 324/715–719, 721, 722, 724, 727, 765, 754, 755, 757, 758, 761, 713; 29/25.01, 592.1, 593, 603.09, 603.1; 438/14, 17, 18; 700/119, 121; 257/48; 73/866.5; 209/571, 573; 414/935–937, 941; 33/503–505

(56) References Cited

U.S. PATENT DOCUMENTS 5,691,648 A * 11/1997 Cheng ........................ 324/715
5,698,989 A    12/1997 Nulman ...................... 324/719
6,435,045 B1 *  8/2002 Chen et al. .................. 324/754

OTHER PUBLICATIONS

Blackburn, David L., "An Automated Photovoltaic System for the Measurement of Resistivity Variations in High-–Resistivity Circular Silicon Slices", Nov. 1979, U.S. Department of Energy, pp. 1–35.*

* cited by examiner

Primary Examiner—Hal Wachsman
(74) Attorney, Agent, or Firm—Maine & Asmus

(57) ABSTRACT

An apparatus for the automated measurement and recording of the electrical resistivity of a semiconductor boule or ingot using the method of four probes has a four point boule support grid is provided adjacent to the home position of a four tip probe which is equipped with three axis linear mobility, rotational capability, and computer control, to provide automated mapping and testing of an "as grown" or ground semiconductor boule with cropped ends, for obtaining and recording resistivity data.

5 Claims, 10 Drawing Sheets

INGOT ID NUMBER: 756851-1
D: \PROJECT\REPORTS
SEMICONDUCTOR TYPE: P
TEMPERATURE DEG C: 21.67
AXIAL POSITION: 0.0000
MAXIMUM RESISTIVITY: 0.0000
CURRENT EXCITATION: 0.0500
04/23/02 10:47:27 AM

| POINT | FORWARD RESISTIVITY | REVERSE RESISTIVITY | AVERAGE RESISTIVITY | RESISTIVITY (23 DEG. C) |
|---|---|---|---|---|
| POINT 1 | 0.006465 | 0.005669 | 0.006067 | 0.006073 |
| POINT 2 | 0.006425 | 0.005492 | 0.005959 | 0.005965 |
| POINT 3 | 0.006437 | 0.005582 | 0.006009 | 0.006015 |
| POINT 4 | 0.006468 | 0.005628 | 0.006048 | 0.006054 |
| POINT 5 | 0.006893 | 0.005328 | 0.006111 | 0.006117 |
| POINT 6 | 0.006244 | 0.005385 | 0.005815 | 0.005821 |
| POINT 7 | 0.006301 | 0.005320 | 0.005811 | 0.005817 |
| POINT 8 | 0.006382 | 0.005452 | 0.005917 | 0.005923 |
| POINT 9 | 0.006328 | 0.005454 | 0.005891 | 0.005897 |
| POINT 10 | 0.006330 | 0.005367 | 0.005848 | 0.005854 |

FIG. 10

APPARATUS FOR AUTOMATICALLY MEASURING THE RESISTIVITY OF SEMICONDUCTOR BOULES BY USING THE METHOD OF FOUR PROBES

This application relates and claims priority to pending U.S. application Ser. No. 60/288,337, filed May 03, 2001.

FIELD OF INVENTION

The invention relates to machines for measuring the electrical resistivity of bulk materials; and in particular to a machine for the automated, multi-point, multi-surface measurement of the resistivity of a semiconductor boule.

BACKGROUND

The four-probe technique to measure electrical resistivity was proposed for semiconductors as early as 1954. This principle of measurement was known much earlier than that and was used to measure the resistivity of the earth. The resistivity of the sample measured is given by the following equation 1, $$\rho = 2\pi s F\left(\frac{V}{I}\right)$$

where:

$\rho$ is the resistivity measured by a collinear four point probe s is the spacing of the probes F is the correction factor V is the measured voltage I is the source current The correction factor accounts for several variables: the thickness of the sample under investigation, location of the probe from the wafer edge, diameter of the sample and location of the current and voltage probes. In addition there is a correction for temperature.

The correction factor depends on the probe spacing to the specimen diameter, the specimen thickness, the slice thickness to probe spacing and the probe tip correction factor. Under the circumstance in which one is not measuring a thin specimen (<1.6 mm) and if the probes are far away from the edge of the specimen which has a large diameter (>16 mm), there would be no correction factor. Equation 1 would reduce to equation 2:

$$\rho = 2\pi s\left(\frac{V}{I}\right)$$

The probes can be spaced in such a way that 2 $\pi$s=1, s being measured in centimeters. The bulk resistivity equation would be simply equation 3:

$$\rho = \left(\frac{V}{I}\right)$$

It is to be noted that temperature plays an important role. Therefore corrections should be made for the measured temperature. It is also important to choose the magnitude of the current to be used for measurement to prevent minority carrier injection as well as localized sample heating.

When measurement of resistivities on boules are made, equation 3 becomes the control equation since one is measuring bulk resistivity at all times.

The measurement of resistivity of semiconductor boules is presently a time-consuming task, difficult to monitor for accuracy of data and position of test points and vulnerable to mistakes.

SUMMARY OF THE INVENTION

It is a goal of the invention to provide an apparatus with a fully automatic measurement system for the four probe measurement and recordation of electrical resistivity characteristics of a semiconductor boule.

It is an objective of the invention to make the fully automatic measurement system adaptable to a production line environment for sequential delivery and removal of boules to a topside boule support grid thereon.

It is a still further objective to make the fully automatic measurement system adaptable to different diameter boules, and to boules of different lengths.

It is another objective to provide the fully automatic measurement system in the form of a shielded apparatus, so as to protect moving parts, cables and hoses as much as possible from exposure to the boule and transport mechanisms.

It is an additional objective to provide a mechanized, multi-point probe head, resistivity sensor system with simple multi-axis motion capability with both linear and rotational components, that can be operated on an automated basis for full cycle surface mapping, resistivity measurements, and recording of all data.

It is still yet another objective to provide an apparatus that provides for centerline movement of a probe head carriage assembly between boule ends and below the boule.

Other goals and objectives within the scope of the invention will be readily apparent to those skilled in the art, from the figures and description of preferred embodiment that follows.

BRIEF DESCRIPTION OF THE FIGURES

FIG. 10 is a representative printout of a ten point resistivity reading, identified by the ID number of the boule to which it applies.

DESCRIPTION OF THE PREFERRED EMBODIMENT

The invention is susceptible of many embodiments. What is illustrated and described is only a preferred embodiment, and not to be construed as limiting of these or such additional claims as may be present in the issued patent.

Figure 1:
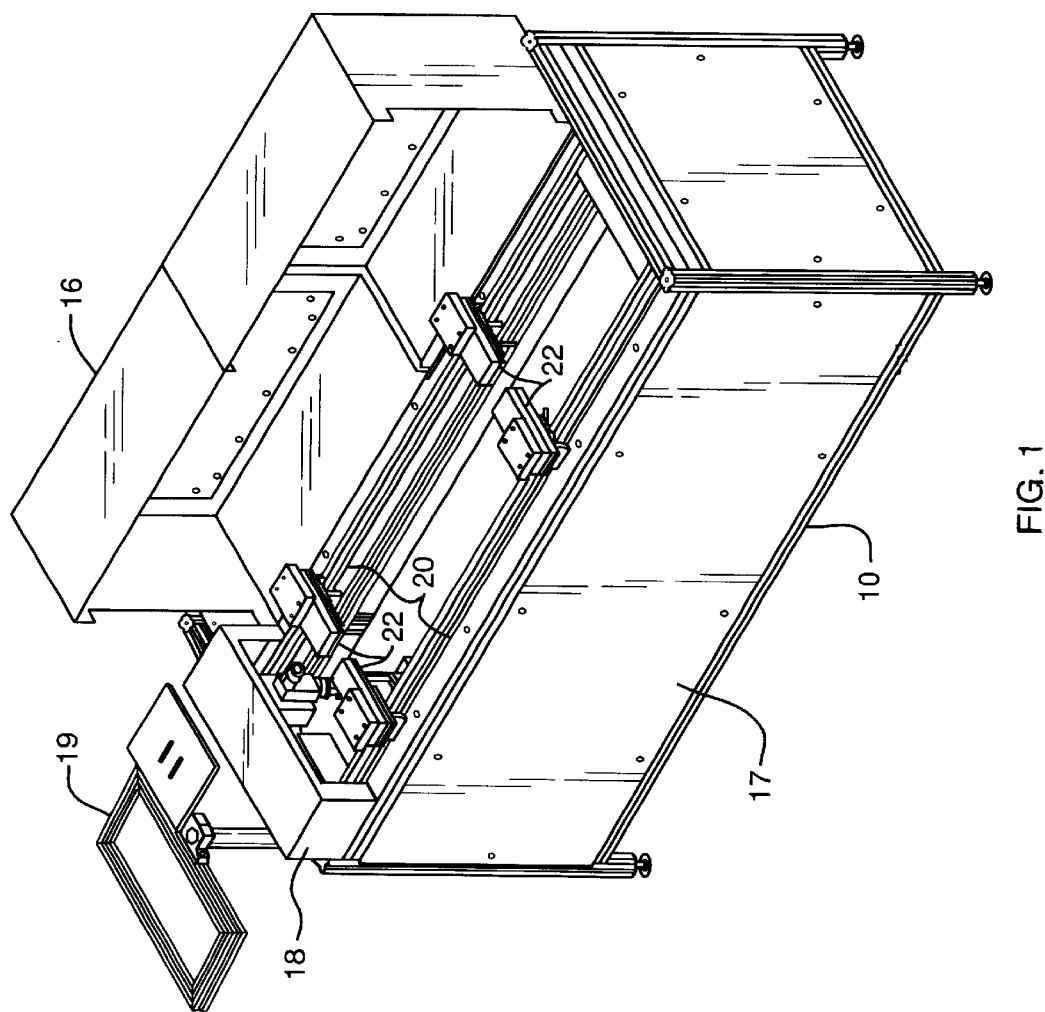
FIG. 1 is an upper right, operator's side, perspective view of a preferred embodiment of the invention, showing the enclosed steel frame, open cover, probe head at the front end of the frame in home position, carriage rails, four boule supports and support rails, and computer and keyboard tray attached to the front end of the frame.
Figure 2:
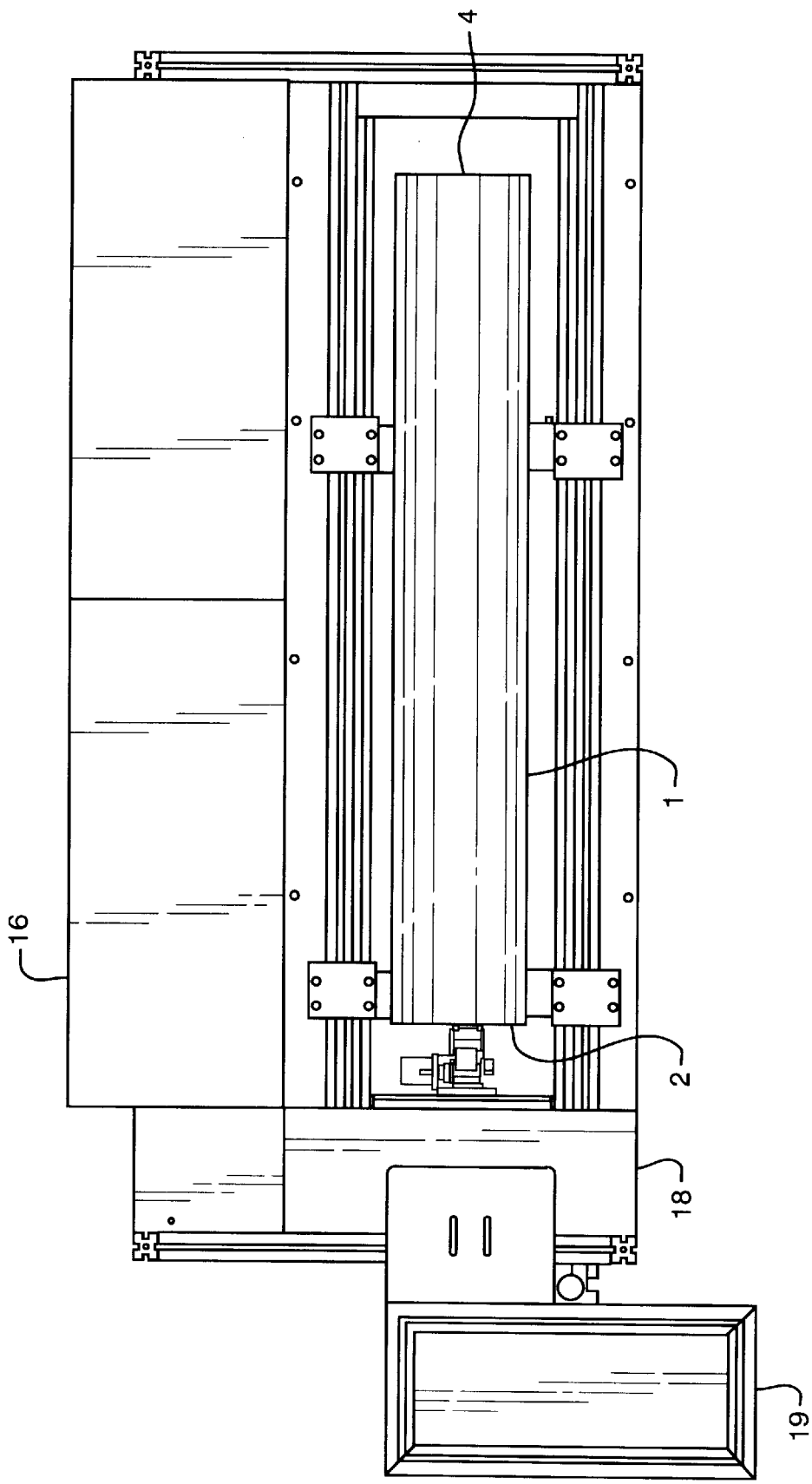
FIG. 2 is top view of the FIG. 1 embodiment, but with a boule in position for being measured and the probe in proximity to the first face end of the boule.
Figure 3:
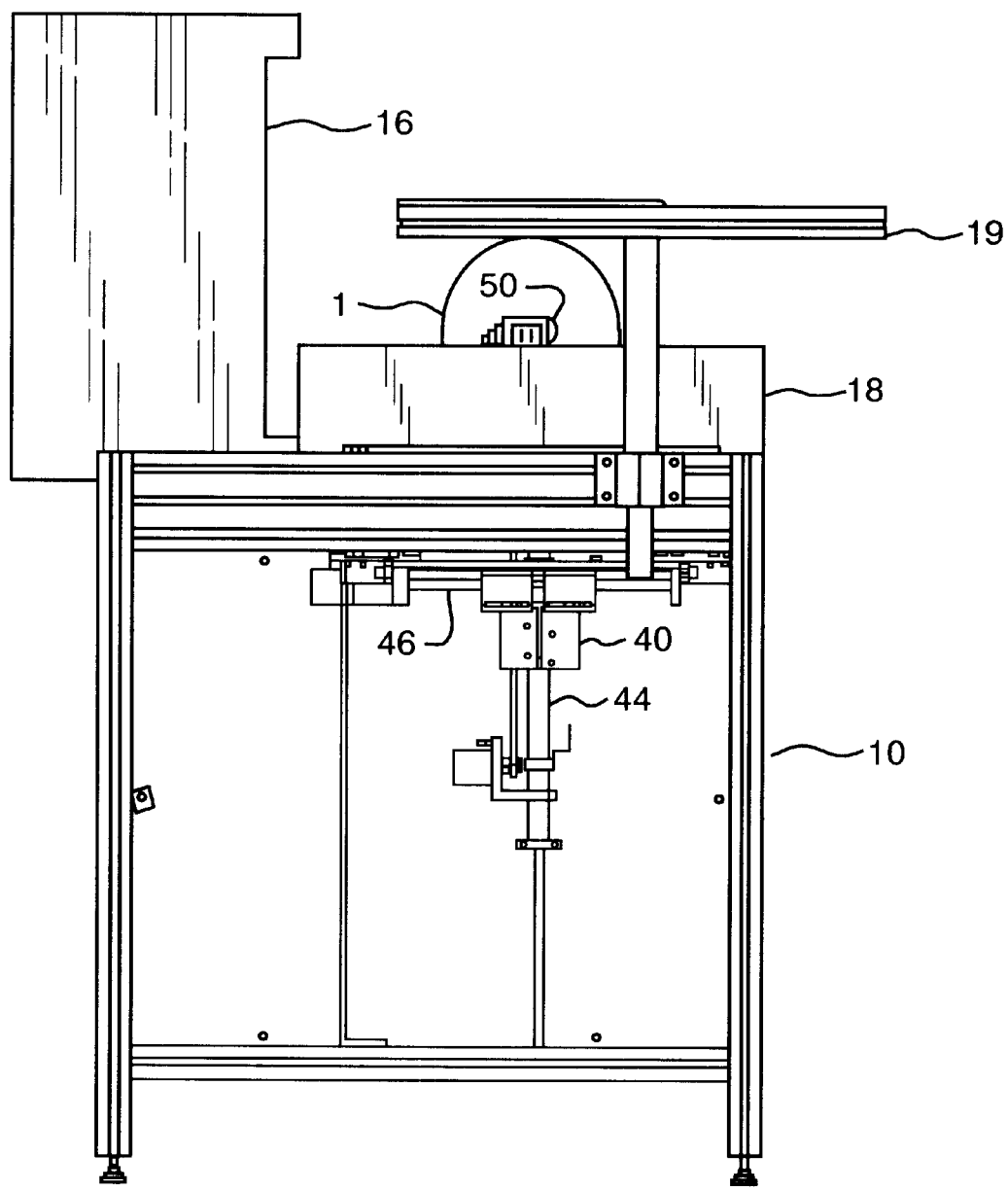
FIG. 3 is a front end elevation of the embodiment of FIG. 1 with the end panel removed but with power and sensor lines and hoses not shown.
Figure 4:
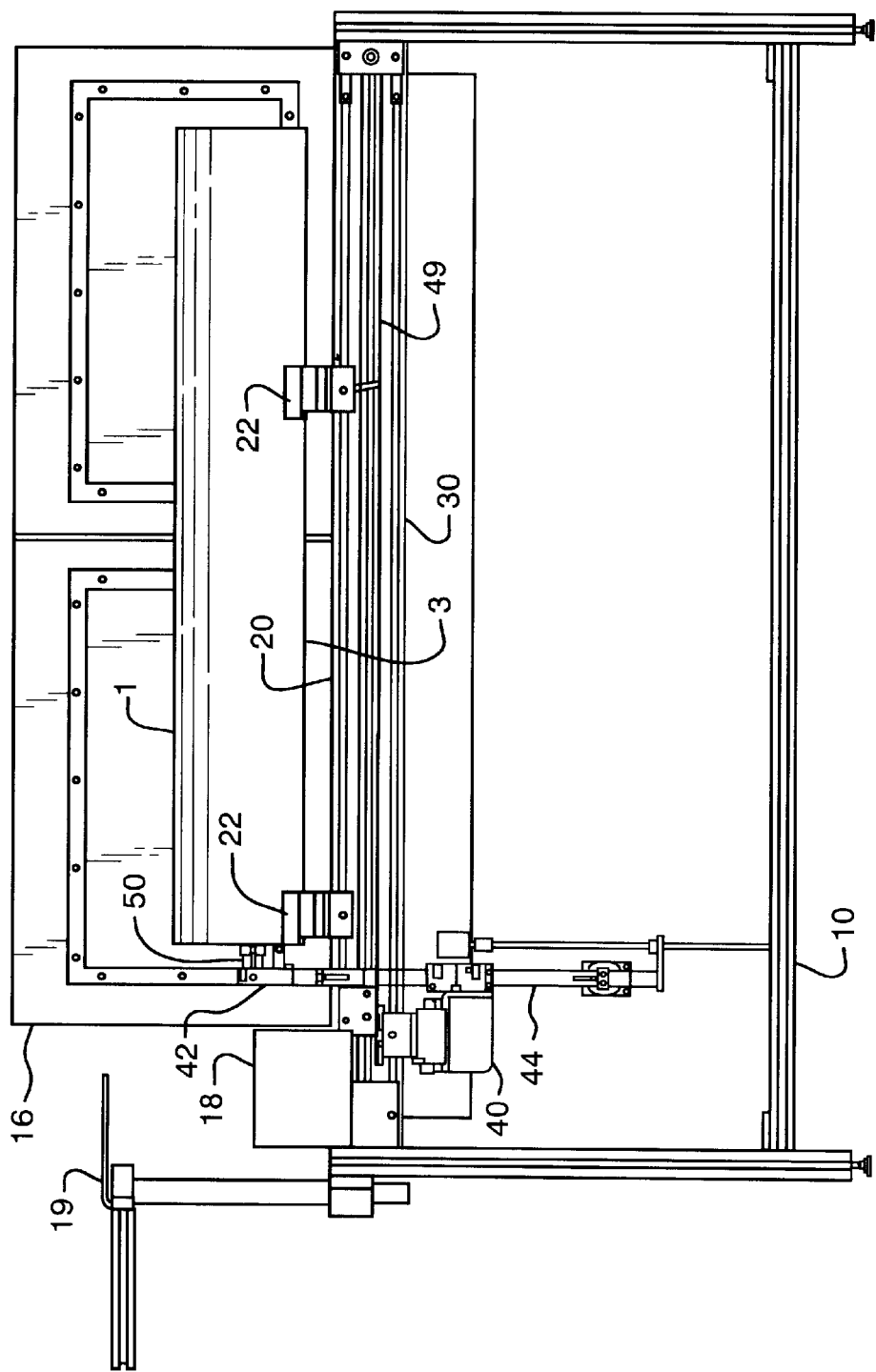
FIG. 4 is an operator's side, elevation of the embodiment of FIG. 1, cover open, panel off, with the probe positioned at the centerpoint of the first face end of a boule as for a resistivity reading.
Figure 5:
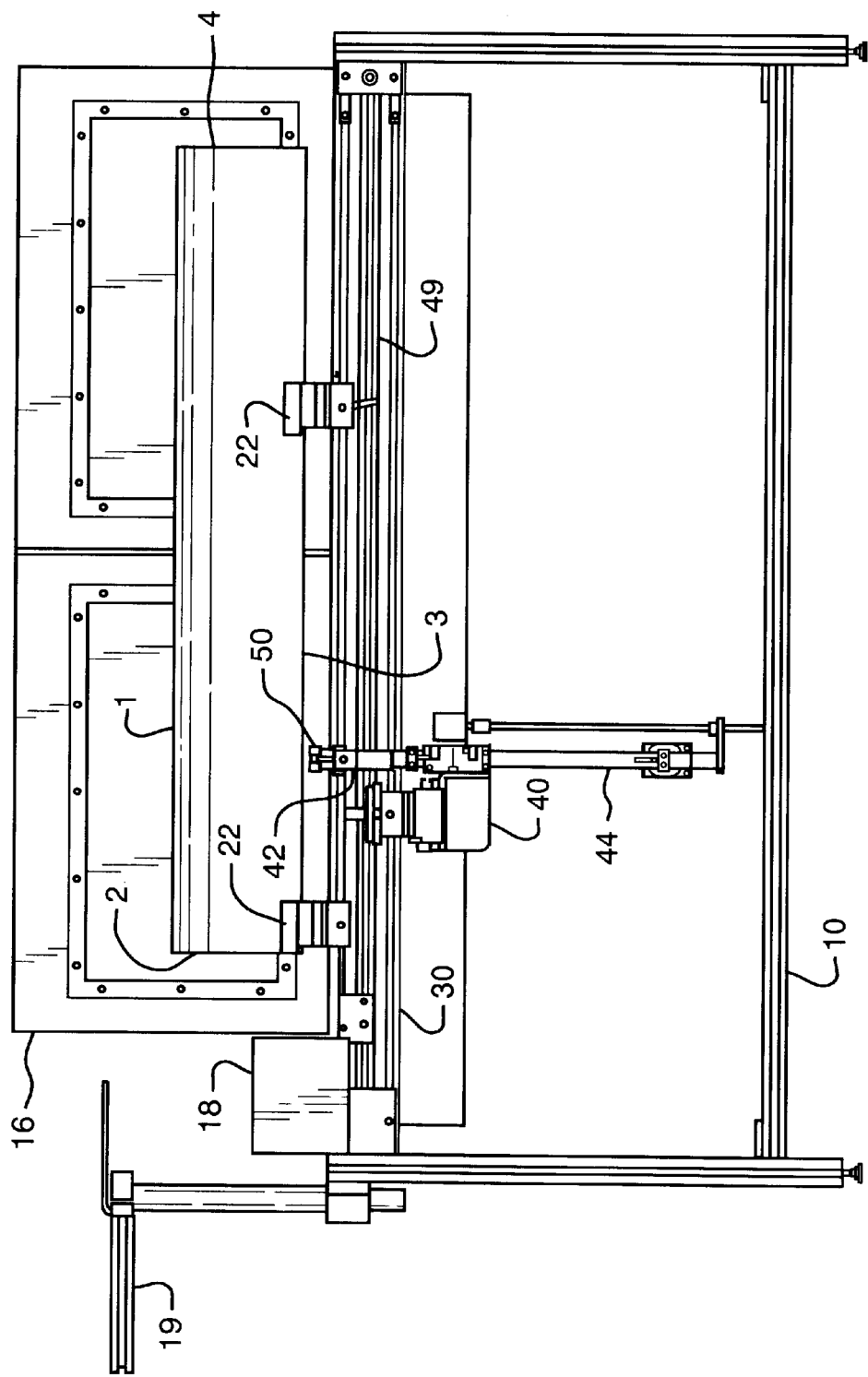
FIG. 5 is an operator's side, elevation of the embodiment of FIG. 4, but with the probe underneath the boule and pointed upward to sense proximity as when traversing from one end to the other.
Figure 6:
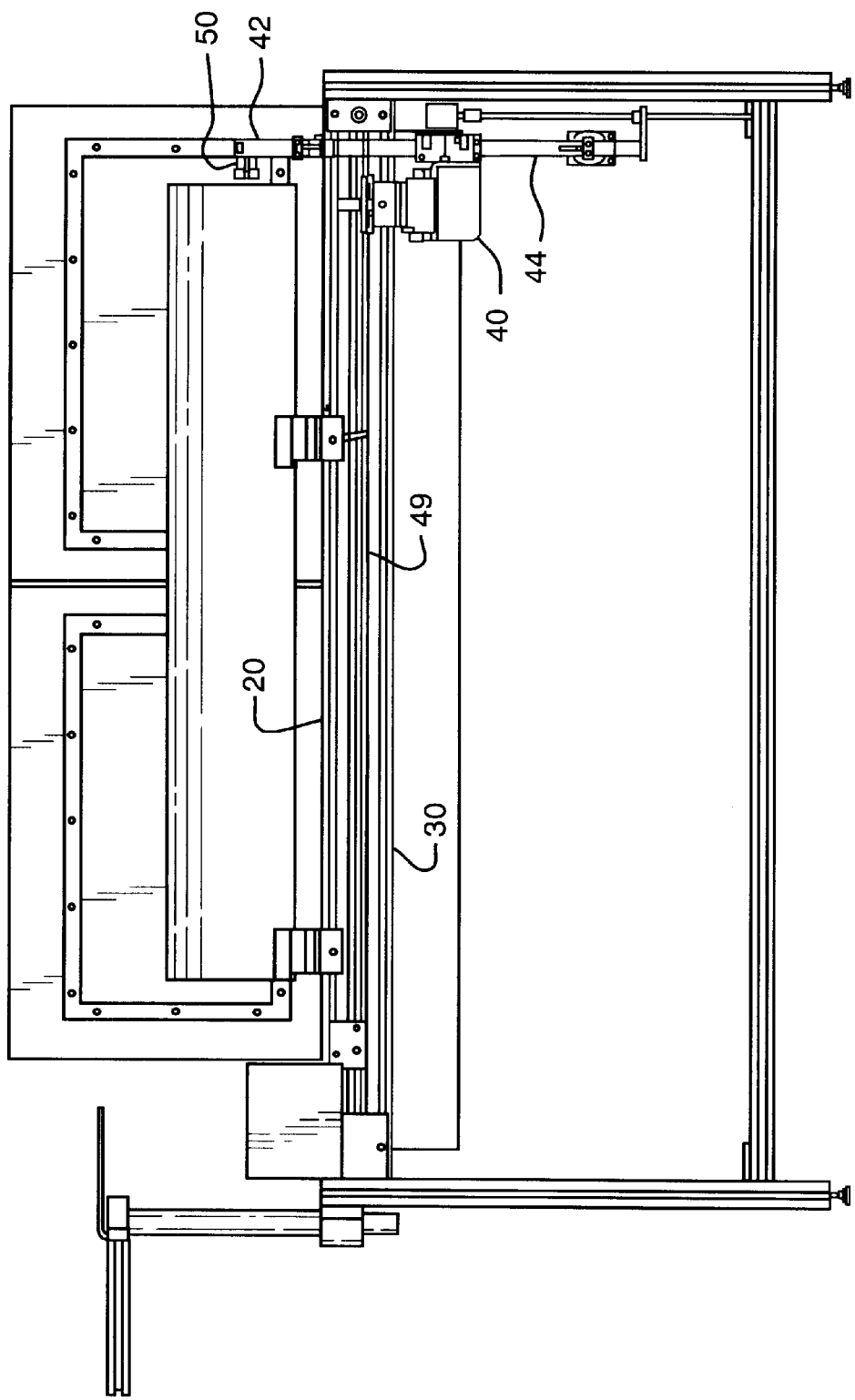
FIG. 6 is another operator's side, elevation of the embodiment of FIG. 4, but with the probe at the centerpoint of the second face end of the boule at the aft end of the frame as for a resistivity reading.
Figure 7:
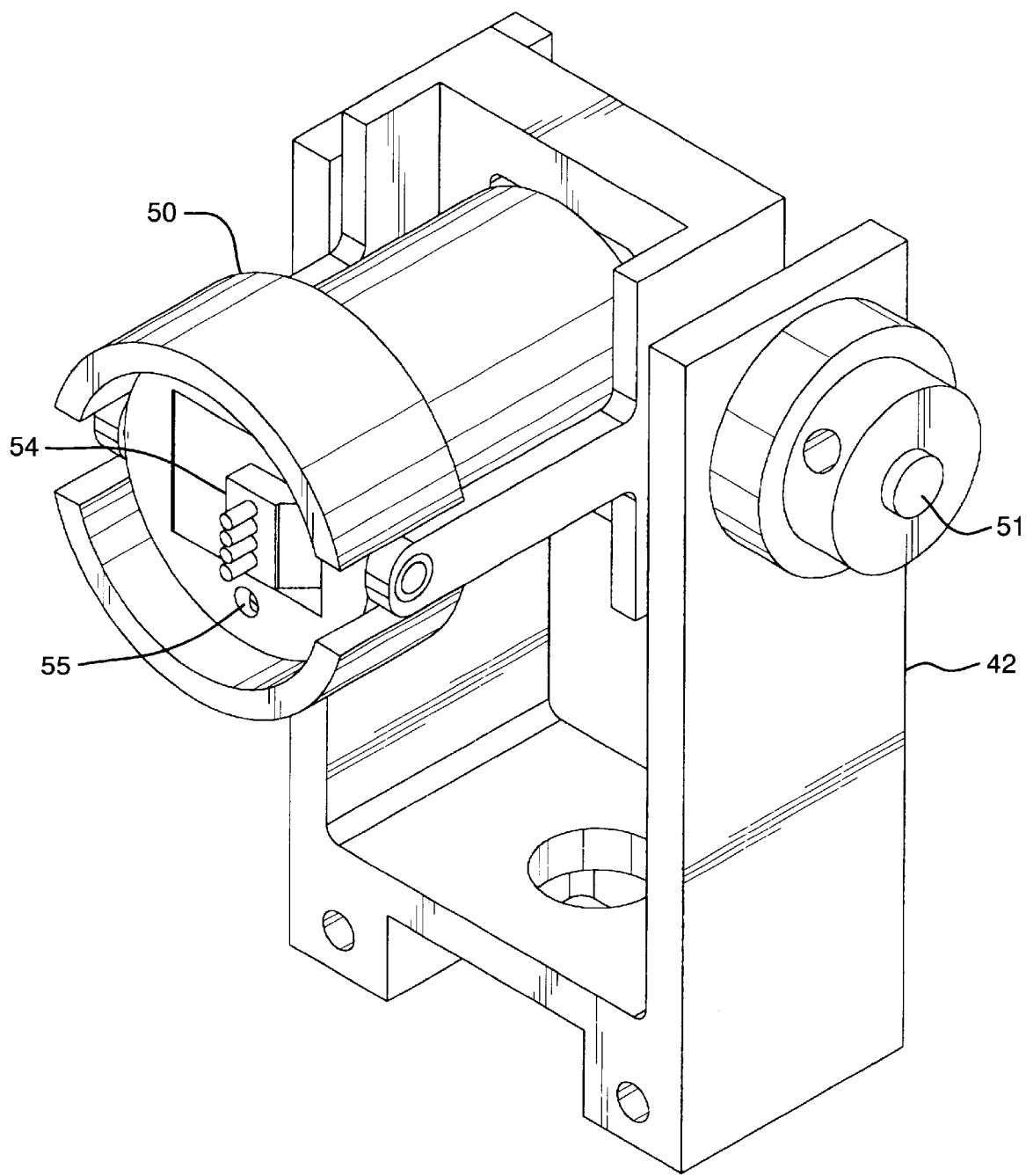
FIG. 7 is a close up perspective view of the probe, probe shaft and pulley, and yoke, with the four point probe head and four probe tips and one of two optical sensors clearly visible on the probe head face.

Referring to FIGS. 1–8, there is shown a preferred embodiment of the fully automatic measurement system of the invention, with enclosure panels 17 on in some figures and removed in others, and cover 16 open. The computer and keyboard tray 19 and the probe home position shroud 18 are at the front end of frame 10. Referring particularly to FIG. 1, there is shown left and right side boule support rails 20. There upon are two front end and two aft end boule supports 22, forming a four point support grid for a boule, as is indicated in other figures.

A semiconductor ingot or boule 1 is shown in position on the four point support grid in other than FIG. 1. Boule 1 is a cylindrical bulk of silicon, in the preferred embodiment up to 51 inches in length, 100 to 200 millimeters in diameter, and weighing up to 300 pounds and more, for which electrical resistivity measurements are required. The boule has a cropped forward or first end surface 2, cylinder sidewall surface 3, and cropped aft or second end surface 4, which are the surfaces upon which the "four probe" method of resistivity measurement is applied. The end surface measurements are referred to as radial resistivity measurements; while the sidewall measurements are referred to as axial resistivity measurements.

Referring in particular to FIGS. 3–6, a probe carriage assembly 40, riding on parallel carriage support rails 30 below boule support rails 20, is comprised of a four point probe head 50 rotatingly mounted in yoke 42 at the top of vertically adjustable post 44, attached by a collar to cross carriage 46, which rides on cross rails 48.

Probe head 50 is configured with a C4S-67™ standard four-point probe 54 with probe spacing 1.55 mm and tungsten carbide probe tips. Probe pressure varies from 70 grams to 180 grams per probe. Four point probe 54 is actuated electrically for resistivity measurements when probe 50 is in the desired position with four point probe 54 in contact with the boule surface.

Probe head rotation is provided by pulley and shaft 51, which is oriented horizontal and parallel to cross rails 48, and at right angles to the lengthwise orientation of frame 10 and carriage support rails 30, so that probe head 50 can be rotated to point upward, or towards either end of frame 10. Motor 52 and probe angle drive belt 53 extending along post 44 to shaft 51, provides for angular position control of probe 50 within yoke 42.

Post 44 is vertically adjustable in the z axis by motorized lead screw 45. Cross carriage 46 is motorized for lateral motion in the y axis along cross rails 48. The complete probe head carriage assembly is motorized and configured with twin, teethed drive belts 49 for movement along the x axis, on probe carriage support rails 30.

Figure 9:
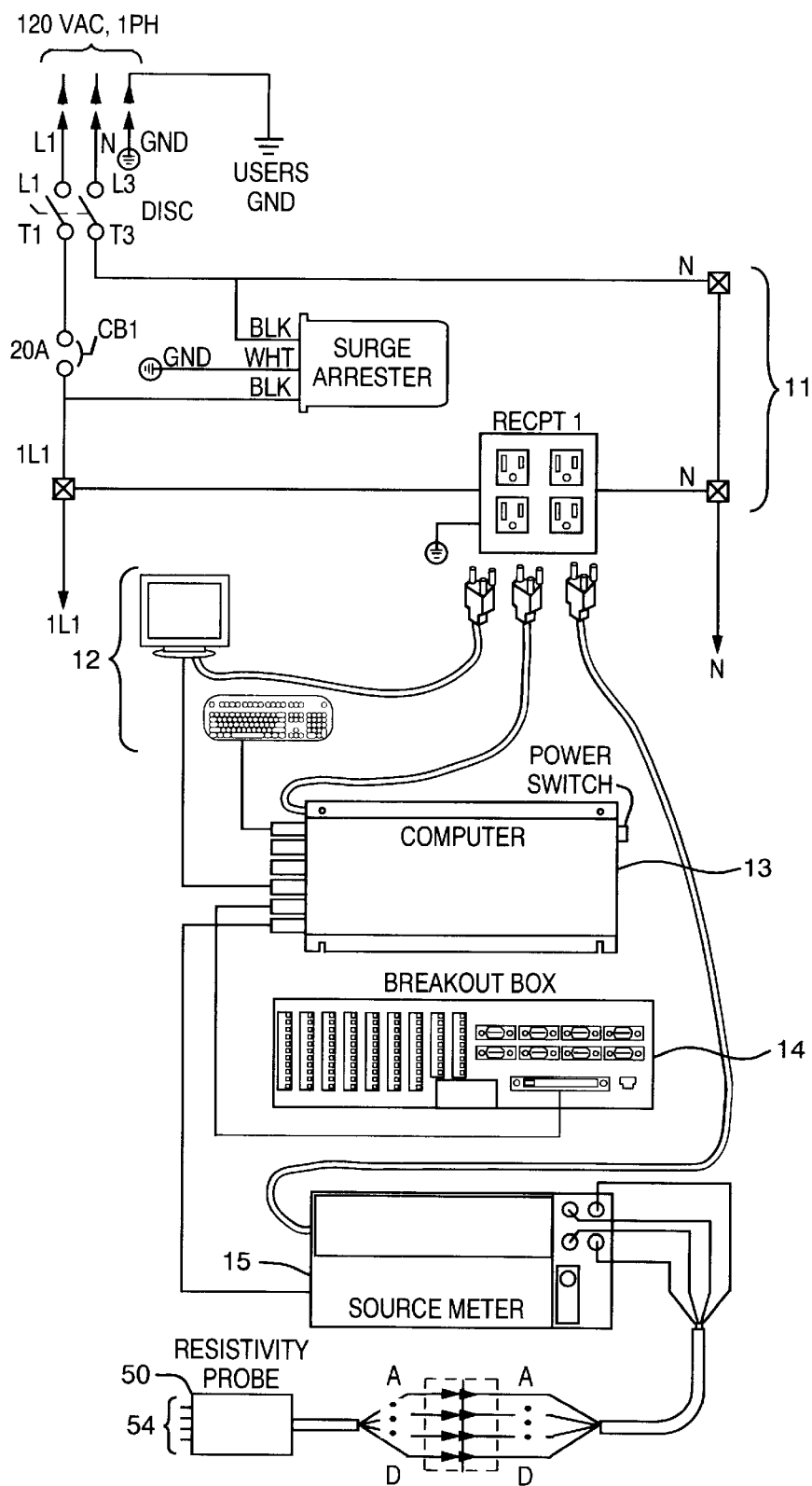
FIG. 9 is a diagrammatic view of the control elements of the embodiment of FIG. 1, with power, computer, breakout box, source meter, and four-point probe illustrated.

The various stepper motors providing motion in the preferred embodiment are controlled by IM483™ micro stepping drives, controlled by a PCI™ Next Move drive control card in computer 13 of FIG. 9. It will be apparent from the above that three axis linear and single axis rotational adjustment are available to probe head 50 by these mechanisms, so that four-point probe 54 can be oriented and operated by computer control for automated surface mapping and sequential resistivity checks on boule 1, first end surface 2; along the underside length of sidewall surface 3; and on second end surface 4. A centerline track of the probe head assembly through frame 10 under the boule simplifies the routing of supporting electrical connections between probe head 50 and respective power and computer control box terminations mounted within or proximate to frame 10.

Without any adjustments, the preferred embodiment can accommodate semiconductor boule diameters of 100 to 200 millimeters (mm). No adjustment, other than to the aft end boule supports 22 in the case of shorter than usual boules, need to be made while maintaining a clear pathway underneath the boule for transiting of probe carriage assembly 40 on carriage rails 30 over the length of the frame without obstructing access to the necessary boule surface areas. The machine frame can be of any useful length, with adequate supports, to accommodate the longest boule, and can be scaled in width for larger and smaller diameter boules if required, as for example up to 300 millimeters or larger.

Boules are introduced to the apparatus by manually controlled or by automated transport mechanisms, by being placed lengthwise onto the boule support grid. It is not required to bring the boule to an exact position; it needs only to be placed with its forward end in the near vicinity of the home position of the probe, with the forward end boule supports 22 having be previously adjusted so as not to extend significantly out from under the usual boule placement position where interference with probe head motion might occur. A computerized probe head mapping sequence provides for automatically locating and measuring the boule within the placement area, as will be further described below.

The four supports 22 for the boule are cantilevered off frame members 20 and cushioned with a non-conductive material, a firm rubber cushion that is configured with a nearly square support edge. The boule rests on a longitudinal outside edge of the rubber cushion on all four supports. The long edge of the rubber form inhibits slippage of the boule, lengthwise in particular, during the measurement cycle. At the same time, due to its x axis orientation, the rubber edge allows the boule to be partially lifted by the operator and rotated easily about its axis if repositioning is required for any reason. A rectangular, four point support grid is especially suitable for a cylindrical form such as a boule, as the cylinder wall is self centering within each of the two end pairs of supports.

The front or forward pair of supports 22, which is closer to the home position of the probe is fixed to coincide with where the boule end is normally placed. The rear or aft end pair of supports 22 are adjustable on rails 20 for lengthwise positioning suitable for the normal length of boules handled, but can be manually repositioned if required, as when the length of the next boule is out of the range of the previous setting. This allows a wide range of length of boules to be handled on the machine. In other embodiments, this adjustment can be automated if boule length is known or is measurable in advance of placement on the support grid.

If much smaller lengths of boules are used, as in the order of a few inches down to about a one and one half inch minimum, a binding strap (not shown) may be attached to forward end supports 22 and manually positioned over the top of the boule and secured to prevent the boule from slipping or tilting during measurements. This optional security measure may also be automated in other embodiments, if shorter boules are the norm.

Referring to FIG. 9, there is connected or mounted to frame 10 a power source 11, operator control/display unit 12, computer processor 13, and interface breakout box 14 connecting the computer processor to various range limit sensors and controllers associated with the probe head motion and carriage functions. There is a source meter 15 for controlling and sensing the current conditions of the four point probe 54 for the resistivity measurements in accordance with the conventional four probe resistivity methodology. There is a fan (not shown) that provides an airflow under slight positive air pressure from a clean air source, when the cover 16 is closed for measurement, to inhibit infiltration of foreign matter into the cabinet during the measurement cycle.

Of the control electronics of this embodiment, computer processor 13 is an industrial computer running on a WINDOWS® NT operating platform. A commercial control software package TEST POINT® (CEC) or LABVIEW® is used with apparatus specific, custom programming to enhance the operator interface and machine operation. Source meter 15 is a high precision programmable constant current KEITILY® source (Model 2400). This model also has a voltage read out facility. Analog to digital interface boards arc used as interface signals from the voltmeter to the computer to a General Purpose Interface Bus (GPIB).

A data entry screen on the operator control/display 12 provides for entering boule identification and other related data for each boule being measured, so that a permanent record of the boule characteristics and resistivity measurements is available for later reference. Computer 13 can be networked in any useful manner to coordinate delivery and removal of boules, receive special operating instructions or boule identification data, and share measurement data.

Measurement

Referring in particular to FIGS. 4–8, to prepare for a resistivity measurement the probe is set automatically to the home position within shroud 18, stowed out of the way as in FIG. 1, before the boule is placed on the table. The home position is arranged during setup to be a couple of inches away from the forward or first end 2 position where the delivery system will normally place the boule or ingot.

The mapping sequence occurs first. On the start command, when cover 16 is sensed to be closed, positive air pressure is sensed, and no other safety lockouts are present, probe 50 is rotated to have four point probe 54 directed towards the expected boule position, and probe carriage 40 is advanced on carriage rails 30 towards face 2 of boule 1 until optical sensors 55 on probe 50 signal proximity of boule face 2, which indicates the lengthwise or X axis location of the first end of the boule. Probe head 50 is then adjusted vertically while sensors 55 are monitored for surface continuity, until the top edge and bottom edge, or Z axis dimensions, of face 2 are established, permitting the computer processor to calculate the boule diameter and the centerpoint.

A logic pattern is then set where the computer processor automatically calculates the current to be used for the boule under test. Probe 50 moves to the center of the boule face and takes a first reading to establish the correct current or "set" current for all measurements on this boule.

After the face 2 lengthwise position, diameter measurement and set current functions are complete, the probe withdraws and moves to the bottom of face 2, the edge of boule 1. Probe head 50 now swings 90 degree upwards and probe carriage 40 moves aft on rails 30, driven by belts 49 below and along the boule. The same two strategically placed laser sensors 55 on probe 50 are used to sense surface proximity and continuity as the carriage is advanced by teethed belts 49 along rails 30. When the continuity ends, the aft end X axis location of the boule is presumed to have been found, thus providing the data for calculating the length of the boule.

Using two sensors 55 reduces the potential for misreading surface continuity in the case where the surface of the boule is not smooth. When the probe head reaches the end of the boule, it is rotated on shaft 51 an additional ninety degrees around towards the boule's aft end or face 4.

The resistivity checks are now initiated. Probe head 50 is elevated and positioned sequentially according to the predetermined recipe. At each position, four point probe 54 is moved forward to make contact with face 4. This is done by a specially spring loaded probe mount on which the four probes are mounted. The probe mount will assure that even if there is a slight taper on the face of the boule, all four probes will make proper contact. A constant current level of electricity, previously determined by the computer control system during the face 2 set current function, is passed through the boule by the outer two probes in the manner known in the art. The voltage that is developed across the inner two probes is measured simultaneously. Then the polarity of the current in the outer probes is reversed. The above procedure is repeated. The arithmetic average of the two ratios of voltage to current, in other words the electrical resistivity as per equation 3, is computed and stored in memory. The probes are retracted for the next probe head movement and measurement.

There are common mapping patterns on the face of the boule that are recommended as per ASTM standards. To map these points on the boule face, the probe has to move to the different required positions on the face of the boule end, such movement being within the three axis motion capability described. Since the center and the diameter is known after the preliminary mapping of the first end 2, the probe can by standard pattern or recipe provided by computer processor 13 move the probe to any of the required points. Resistivity readings can be taken at all points and data logged in the control computer or remotely. If the user so requires, the system can be programmed to map other than industry standard patterns. For user defined positions, a recipe is first generated. This is done by defining the number of points to be mapped, and converting the points to be mapped into polar coordinates. The recipe is stored in a recipe file which can be accessed by the program. The resistivity measurements are done as described, such as on the center alone, or at five points or nine points or as otherwise may be required and programmed. After the face 4 measurements, if axial resistivity is not required, the probe is returned to its home position.

If the resistivity on the axis of the boule is to be measured via surface measurements on the sidewall surface, the boule has generally been surface ground earlier to obtain a uniform diameter and wall surface. If starting from home position, the probe moves from its home position and locates the face of the boule as previously described. The probe then slides below the boule starts moving along the sidewall surface below the boule, again as previously described. At preprogrammed positions lengthwise of the boule, the four point probe 54 is elevated and measures the resistivity at that point. It then drops back and moves to the next point along the length of the boule, and makes the measurement again and so on.

If the axial resistivity is to be done concurrently with a radial measurement cycle, it is done after measuring the resistivity on face 4 of the boule. Having already measured the length of the boule using sensors 55 on the probe head during the motion from the front end to the aft end of the boule, computer processor 13 has the information from which to calculate the number of points, spacing and position for the sidewall measurements for axial resistivity. The operator can specify a different or additional number of readings if desired. Four point probe head 54 is elevated at the prescribed points along the underside surface 3 of boule 1 while probe 50 is traversed back towards the front end of the frame and its home position. As before, all data is logged automatically.

As described above, all cables, and lines for moving the probe carriage and activating the probe, and belts 49 and 53 and vertical lead screw 45 are neatly arranged below the boule and within frame 10 and its enclosure panels. Frame 10 is normally nearly fully enclosed. The only visibility into the working parts of the apparatus is through the slot between rails 20 through which probe 50 moves lengthwise below the boule and in the vicinity of the boule end faces.

As described above, proximity sensors 55 are optical sensors that signal proximity of the probe 50 to the boule surface. The preferred embodiment also has several induction sensors (not shown) connected to the motor controller breakout box 14 and monitored via the program running on computer processor 13. Among them are a Home Position Sensor that signals a home position for the rotation of the probe on shaft 51. When this sensor is triggered the probe rotation is at its rotational component of home position. Home position also requires cross carriage 46 be at the centerline with respect to the Y axis, and typically at lower range Z axis and at the front end limit of the X axis. X Axis Sensors signal when the probe carriage is at either the front or aft end limit of lengthwise travel on rails 20. Y Axis Sensors signal Y axis limit positions of the probe head cross carriage 46 on probe carriage 40. Z Axis Sensors signal when the probe head is at its upper or lower vertical limits.

Other digital signals from the software are routed through source meter 15 to activate the pneumatics that move the probe heads. Servo motor movements to move the probe in the three axis are also controlled by the software. Data logging is achieved in a suitable database format. Depending on the semiconductor type (p type or n type) of the crystal and the ambient temperature (T), corrections of the resistivity calculations have to be made to read resistivity at 23° C. as required by ASTM standards. For this purpose, an air temperature sensor is incorporated into the apparatus and connected to the computer, and the ASTM (F84–93) standards temperature coefficient ($C_T$) table is built into the computer. With the use of a lookup table correction factors are generated and temperature correction factor ($F_T$) is calculated using the formula $$F_T = 1 - C_T (T-23)$$

The resistivity corrected to 23° C. is given by $$\rho(23) = \rho(T) \times F_T$$

The resistivity units are measured in ohm.cm.

Figure 8:
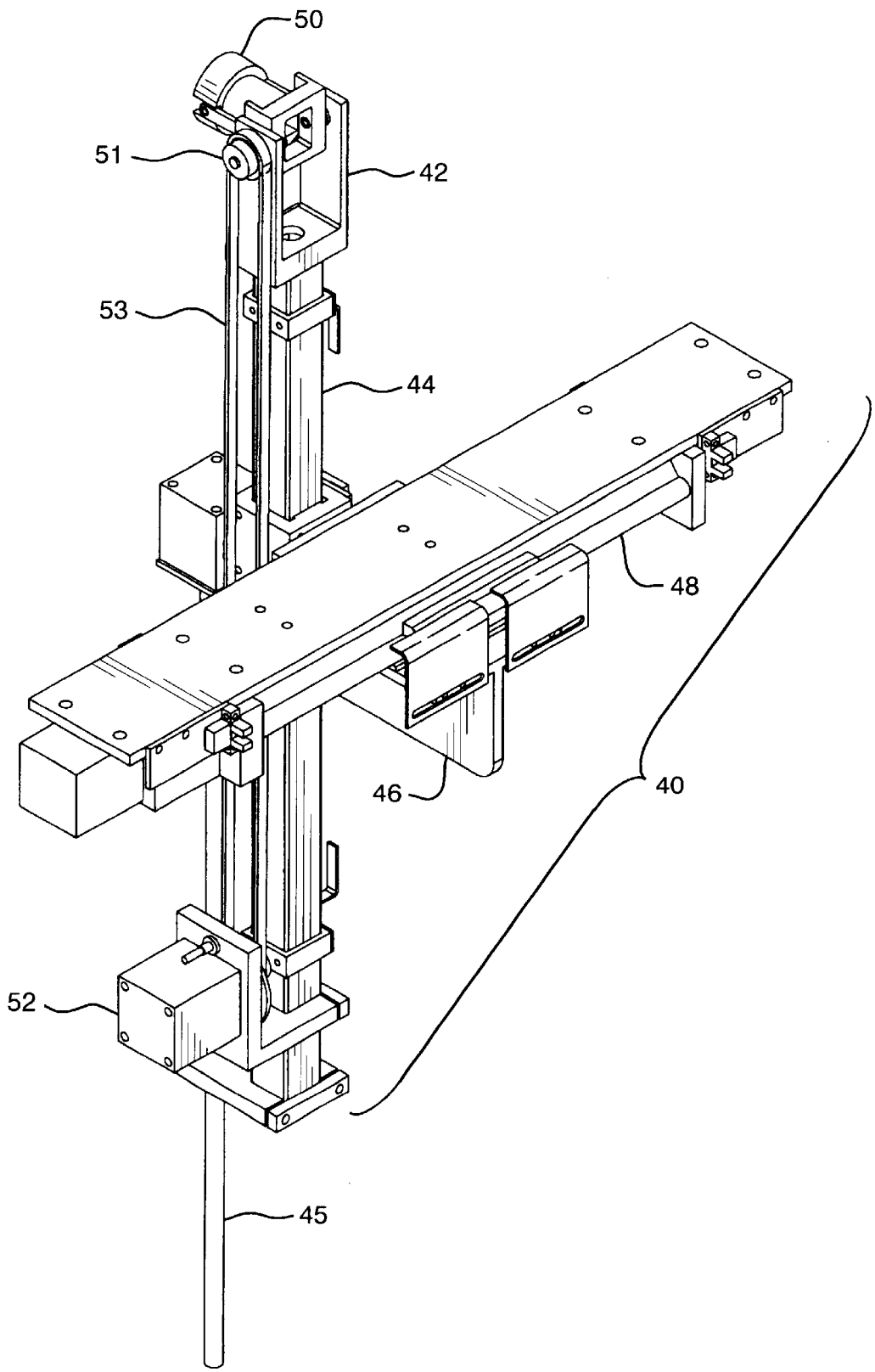
FIG. 8 is a perspective view of the probe mounted on the probe carriage assembly of the preferred embodiment, with belt driven rotational motion for the probe, and vertical and crosswise linear motion incorporated directly into the probe carriage, which gets lengthwise linear motion by riding on lengthwise rails in the frame underneath the boule support rails.

The data produced by the automated performance of the apparatus may be printed in the form of a report, as illustrated by the example of FIG. 8, where an actual ten point resistivity measurement, including forward, reverse and average resistivity, and temperature corrected resistivity, of a boule identified with an Ingot ID Number is documented.

The computer is fully equipped with networking capabilities. Data can be stored in several different formats and analyzed. Operators are warned if the readings are out of range. Automatic voltage limit lockouts are provided if the high voltages are sensed due to improper contacts or large resistance when the probes contact the boule. Emergency switches are provided on the machine for the operator to stop operations at any time. Controls to move the probe away are then facilitated by manual operations using controls on the screen. If no boule is placed on the machine and operations are started, the machine will record an error message and will not proceed further.

The full implementation of the preferred embodiment can be readily accomplished without inventive effort by those skilled in the requisite arts, upon review of this specification and the attached figures.

Other variations and embodiments are within the scope of the invention. For example, there may be different types or additional proximity sensors for detecting and mapping the surface area of the boule, and other sensors significant to the resistivity measurement process. There may be various other means for generating the three axis and rotation motions described, such as an industrial robot with a four point probe attached at its tool head. There may be another axis of rotation for the probe head, parallel to the axis of the boule, such that the four point probe 54 orientation can be rotable with respect to the end face, or that that sidewall measurements can be taken at points radially offset somewhat from the underside surface centerline of the boule.

As another example, there is an automated measurement system for measuring resistivity of semiconductor boules according to a four probe methodology, consisting of a four point probe with a home position, where the probe is configured with three axis linear motion capability and at least one axis rotation capability, where the linear motion capability and the rotation capability are connected to a power source and controlled by a computer processor for departing from and returning to the home position. The four point probe is connected to a current source and a voltage sensor according to four probe methodology, and is further connected to and controlled by the computer processor.

There is a boule support grid for supporting a boule with a first face end and a second face end in a horizontal orientation with the first face near the home position, and with the first face and the underside surface centerline and the second face exposed for access by and within reach of the four point probe through its three axis motion capability.

There is at least one boule surface sensor on the four point probe, preferably a laser sensor, for detecting proximity of the four point probe to any surface of the boule. The computer processor has program steps for directing a boule locating sequence by the four point probe and sensor beginning from the home position and exploring the first face and the underside surface centerline and the second face of the boule, and for deriving the boule diameter and boule length from the data acquired from exploring the boule surfaces.

The computer processor has program steps for testing a selected point on said boule with the four point probe and calculating a set current according to four probe methodology. The computer processor has program steps for conducting radial resistivity measurements with the four point probe of at least one face of the boule. The computer processor also has program steps for conducting axial resistivity measurements of the underside surface centerline of the boule.

The system may have a frame with spaced apart parallel boule support rails, where the boule support grid is made up of fore and aft end boule supports attached to each boule support rail so as to form a four point support grid, with the fore end boule supports located near the probe's home position.

The system may have a probe carriage to which the probe is attached, where the probe carriage has three axis linear motion capability; the three axis linear motion consisting of lengthwise of the frame as X axis, crosswise of the frame as Y axis and vertical motion as Z axis. The four point probe may be mounted by a probe shaft on a Z axis adjustable support post on the probe carriage. The frame may have at least one X axis carriage rail, and preferably two parallel rails, upon which the probe carriage travels. The probe carriage may have at least one Y axis rail, and preferably two rails, upon which the probe cross carriage and four point probe travels. The probe's rotational capability may be provided by a probe shaft in a yoke. The system may have stepper motors connected to and controlled by the computer processor for rotating and moving the four point probe and moving the probe carriage.

The computer processor may be connectable or connected to a computer network. The system may be cooperatively operated with an automated system of sequential delivery and removal of boules as in a production environment. The system may be substantially enclosed and have a cover closable over a boule on the support grid. There may be an air temperature sensor communicating with the computer processor. There may be positive pressure airflow source into the enclosed system.

The steps for directing a boule locating sequence by the four point probe and sensor from home position to first end face and to the underside surface centerline and to the second end face, and for deriving boule face diameter and centerpoint and boule length from that data, may include: beginning with the four point probe in the home position and pointed towards the boule support grid where the boule is expected to be; and advancing the four point probe from home position on centerline of the boule support grid towards the first face end until the probe sensor indicates proximity to the first face of the boule, thereby indicating X axis location of said first face.

Then vertically moving the four point probe upward along the first face until the sensor indicates loss of proximity, thereby indicating the upper Z axis edge of the first face; vertically moving the four point probe downward along the first face until the sensor indicates loss of proximity, thereby indicating the lower Z axis edge of said first face; and from that calculating the boule face diameter and centerpoint.

Then rotating the four point probe to point upward; lowering the probe to below the lower Z axis edge of the first face; advancing the probe carriage along the Z axis a short ways to place the probe beneath the near end of the boule; vertically moving the four point probe upward until the sensor indicates proximity to the underside surface of the boule; and further advancing the probe carriage on the X axis along the underside surface until the sensor indicates loss of proximity, thereby indicating the X axis location of the second face of the boule. Then calculating the boule length from the X axis location of the first face and second face.

The steps for testing a selected point on the boule with the four point probe and calculating a set current according to four probe methodology may include the steps: beginning with the four point probe proximate the first face as indicated by the sensor; moving the four point probe to the centerpoint location on the first face; advancing the probe tips of four point probe into contact with the first face; applying a predetermined test current and sensing a response voltage; and calculating there from a suitable set current for the resistivity testing of the boule according to four probe methodology.

The steps for conducting radial resistivity measurements with a four point probe of at least one face of the boule may include the steps: beginning with the four point probe proximate the face as indicated by the probe sensor; moving the four point probe along the face to a first radial measurement position of a predetermined face pattern of resistivity measurements; advancing the probe tips of the four point probe into contact with said face; applying the set current and sensing a response voltage; and calculating there from a radial resistivity value according to four probe methodology; and repeating the above steps for additional radial measurement positions of the selected pattern until all positions are measured.

The steps for conducting axial resistivity measurements with the four point probe of the underside surface centerline of the boule may include: beginning with the four point probe proximate the underside surface centerline as indicated by the probe sensor; moving the four point probe along the surface centerline to a first axial measurement position of a predetermined pattern of axial resistivity measurements; advancing the probe tips of the four point probe into contact with the face; applying the set current and sensing a response voltage and calculating there from a radial resistivity according to four probe methodology; and repeating these steps for additional axial measurement positions until all positions of the selected pattern are measured.

The program steps of the computer processor may include: making a record of boule diameter, boule length, and resistivity measurements for each boule; and identifying each record with its respective boule. The computer processor may be networked for transfer of records to other locations.

As yet another example, there may be a measurement apparatus for use with a computer processor for the automated measuring of resistivity of semiconductor boules according to a four probe methodology, consisting all of the hardware described in the above embodiment but without a computer processor, while being connectible to such a computer processor or equivalent process controller capability, for all sensory outputs and all control inputs required to operate the apparatus for its intended purpose, where the computer processor is capable of implementing an automated sequence of four probe resistivity measurements utilizing the capability of the hardware as described.

The description above and figures attached provide a fully enabling disclosure of a preferred embodiment of the invention, as will be readily apparent to those skilled in the art. The claims that follow are illustrative but not exhaustive of the scope of the invention disclosed, and should be read accordingly.

What is claimed is:

1. A measurement apparatus for use with a computer processor for the automated measuring of resistivity of semiconductor boules according to a four probe methodology, comprising a four point probe having a home position and being movable along three axes and rotatory around at least one axis for departing from and returning to said home position, said four point probe connected to a power source and connectible to said computer processor, said four point probe connected to a current source and a current sensor according to said four probe methodology, and further connectible and controllable by said computer processor, a boule support grid for supporting a boule with a first face end and a second face end in a horizontal orientation with said first face end near said home position, and with said first face end and the underside surface centerline and said second face end exposed for access by and being within reach of said four point probe, at least one boule surface sensor on said four point probe for detecting proximity of said four point probe to a surface of said boule.

2. A measurement apparatus for use with a computer processor for the automated measuring of resistivity according to claim 1, further comprising a frame with spaced apart parallel boule support rails, said boule support grid comprising fore and aft end boule supports attached to each said boule support rail so as to form a four point support grid, said fore end boule supports located proximate said home position.

3. A measurement apparatus for use with a computer processor for the automated measuring of resistivity according to claim 2, said apparatus further comprising a probe carriage to which said four point probe is attached, said probe carriage being movable along three axes, said three axes comprising lengthwise of said frame motion as X axis, crosswise of said frame motion as Y axis and vertical motion as Z axis motion, said four point probe being mounted by a probe shaft on a Z axis adjustable support post on said probe carriage, said frame further comprising at least one X axis carriage rail upon which said probe carriage travels, said probe carriage having at least one Y axis rail upon which said four point probe travels, said at least one axis rotational capability centered on said probe shaft, said apparatus further configured with stepper motors connectible to said computer processor for rotating and moving said four point probe and moving said probe carriage.

4. A measurement apparatus for use with a computer processor for the automated measuring of resistivity according to claim 3, said apparatus being substantially enclosed and having a cover closable over a boule on said boule support grid, said apparatus further comprising an air temperature sensor connectible to said computer processor, and a positive pressure airflow source.

5. A measurement apparatus for use with a computer processor for the automated measuring of resistivity according to claim 4, said apparatus capable of holding and measuring boules ranging from 1.5 to 51 inches in length and from 100 to 300 millimeters in diameter.

* * * * *